US011672957B2

(12) United States Patent
Dant et al.

(10) Patent No.: US 11,672,957 B2
(45) Date of Patent: Jun. 13, 2023

(54) RESILIENT TIP AND METHOD

(71) Applicants: Heraeus Medical Components LLC, St. Paul, MN (US); Heraeus Deutschland GmbH & Co. KG, Hanau (DE)

(72) Inventors: Jack Dant, St. Paul, MN (US); Mark Erie, Chaska, MN (US); David Johnson, Saint Louis Park, MN (US); Trent Birkholz, Excelsior, MN (US); Douglas Pletcher, Minneapolis, MN (US); Jason Albers, Crystal, MN (US); Michael Grimm, Bad Vilbel (DE)

(73) Assignees: Heraeus Medical Components LLC, St. Paul, MN (US); Heraeus Deutschland GmbH & Co. KG, Hanau (DE)

(*) Notice: Subject to any disclaimer, the term of this patent is extended or adjusted under 35 U.S.C. 154(b) by 302 days.

(21) Appl. No.: 16/045,950

(22) Filed: Jul. 26, 2018

(65) Prior Publication Data
US 2019/0030300 A1 Jan. 31, 2019

Related U.S. Application Data

(60) Provisional application No. 62/643,929, filed on Mar. 16, 2018, provisional application No. 62/537,162, filed on Jul. 26, 2017.

(51) Int. Cl.
*A61M 25/09* (2006.01)

(52) U.S. Cl.
CPC ... *A61M 25/09* (2013.01); *A61M 2025/09075* (2013.01); *A61M 2025/09108* (2013.01); *A61M 2025/09141* (2013.01); *A61M 2025/09175* (2013.01); *A61M 2205/0266* (2013.01); *A61M 2207/00* (2013.01)

(58) Field of Classification Search
CPC .............................. A61M 25/09–0905; A61M 2025/09008–09191; A61M 2025/0177; A61B 5/6851; A61B 2017/22038–22045
See application file for complete search history.

(56) References Cited

U.S. PATENT DOCUMENTS

| 5,108,368 | A | * | 4/1992 | Hammerslag ..... A61M 25/0147 604/95.04 |
| 5,111,829 | A | | 5/1992 | Alvarez de Toledo |
| 5,341,818 | A | | 8/1994 | Abrams et al. |
| 5,368,049 | A | | 11/1994 | Raman et al. |
| 5,402,799 | A | | 4/1995 | Colon et al. |
| 5,637,089 | A | | 6/1997 | Abrams et al. |

(Continued)

FOREIGN PATENT DOCUMENTS

| EP | 0515201 | 11/1992 |
| EP | 0868924 | 10/1998 |

(Continued)

*Primary Examiner* — Etsub D Berhanu
*Assistant Examiner* — Samuel C Kim
(74) *Attorney, Agent, or Firm* — Dicke, Billig & Czaja, PLLC

(57) ABSTRACT

One aspect is a medical guidewire including a core wire with a proximal end extending out to a distal end and a resilient portion coupled to the distal end of the core wire at a distal tip section of the guidewire. The resilient portion includes a superelastic material.

14 Claims, 3 Drawing Sheets

(56) References Cited

U.S. PATENT DOCUMENTS

| | | | | |
|---|---|---|---|---|
| 5,695,111 | A | 12/1997 | Nanis et al. | |
| 5,769,796 | A * | 6/1998 | Palermo | A61M 25/09 600/433 |
| 5,916,178 | A | 6/1999 | Noone et al. | |
| 5,993,424 | A | 11/1999 | Lorenzo et al. | |
| 6,165,292 | A | 12/2000 | Abrams et al. | |
| 6,280,539 | B1 | 8/2001 | Abrams et al. | |
| 6,375,629 | B1 | 4/2002 | Muni et al. | |
| 6,461,453 | B1 | 10/2002 | Abrams et al. | |
| 6,488,637 | B1 * | 12/2002 | Eder | A61M 25/09 600/585 |
| 6,544,197 | B2 | 4/2003 | DeMello | |
| 6,602,228 | B2 | 8/2003 | Nanis et al. | |
| 6,638,372 | B1 | 10/2003 | Abrams et al. | |
| 6,682,608 | B2 | 1/2004 | Abrams et al. | |
| 7,244,319 | B2 | 7/2007 | Abrams et al. | |
| 7,258,753 | B2 | 8/2007 | Abrams et al. | |
| 7,747,314 | B2 | 6/2010 | Parins et al. | |
| 7,947,012 | B2 | 5/2011 | Spurchise et al. | |
| 7,993,286 | B2 | 8/2011 | Reynolds et al. | |
| 8,221,387 | B2 | 7/2012 | Shelso et al. | |
| 8,222,566 | B2 | 7/2012 | Shireman et al. | |
| 8,308,658 | B2 | 11/2012 | Albers et al. | |
| 8,414,506 | B2 | 4/2013 | Reynolds et al. | |
| 8,500,658 | B2 | 8/2013 | Boyle et al. | |
| 8,585,612 | B2 | 11/2013 | Nishigishi | |
| 2002/0049392 | A1 | 4/2002 | Demello | |
| 2003/0069521 | A1 * | 4/2003 | Reynolds | A61M 25/09 600/585 |
| 2006/0064055 | A1 * | 3/2006 | Pile-Spellman | A61M 25/0105 604/95.05 |
| 2009/0118644 | A1 * | 5/2009 | Skujins | A61M 25/09 600/585 |
| 2011/0015618 | A1 | 1/2011 | Satou et al. | |
| 2011/0054351 | A1 | 3/2011 | Fox et al. | |
| 2015/0094616 | A1 | 4/2015 | Simpson et al. | |
| 2015/0314109 | A1 | 11/2015 | Minar et al. | |
| 2016/0038719 | A1 | 2/2016 | Asmus | |
| 2016/0136396 | A1 | 5/2016 | Chludzinski et al. | |

FOREIGN PATENT DOCUMENTS

| | | |
|---|---|---|
| EP | 0879617 | 11/1998 |
| EP | 1464358 | 10/2004 |
| EP | 2361652 | 8/2011 |
| EP | 2211967 | 7/2015 |
| WO | 2006002199 | 1/2006 |
| WO | 2012058302 | 5/2012 |

* cited by examiner

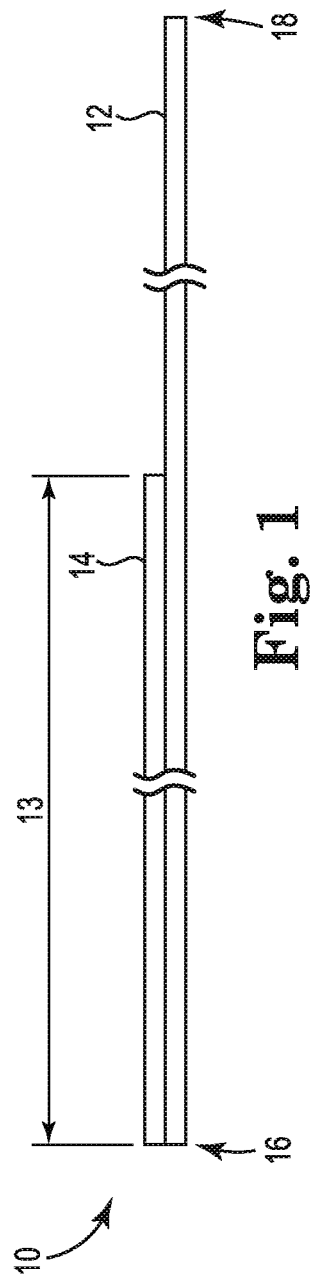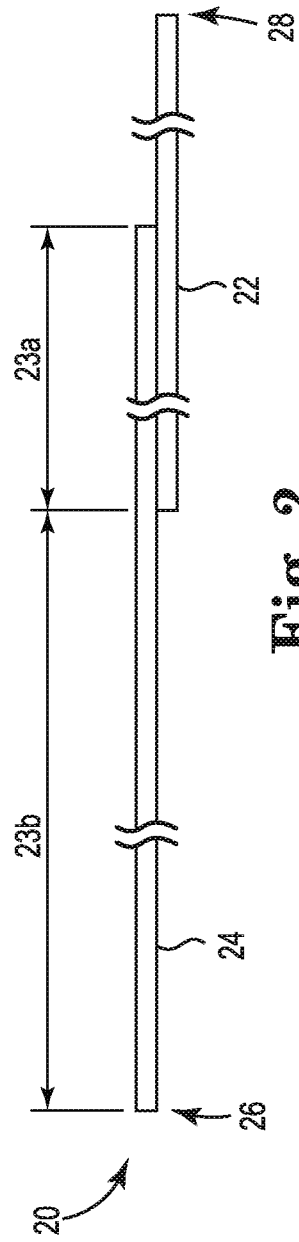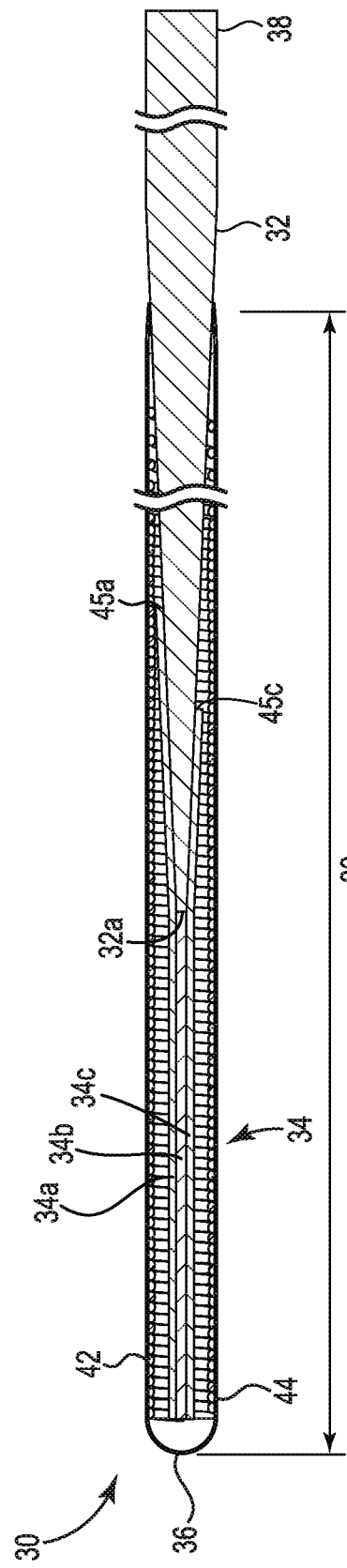

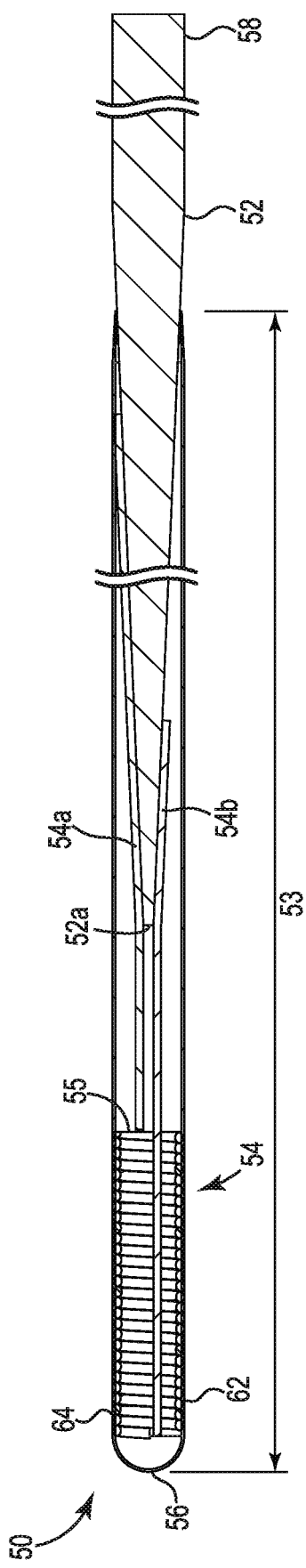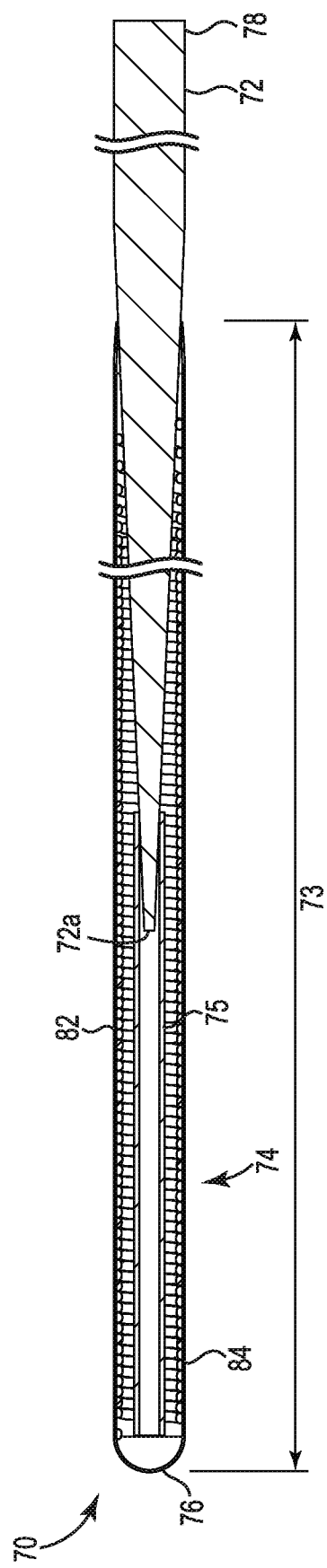

RESILIENT TIP AND METHOD

CROSS-REFERENCE TO RELATED APPLICATION

This Non-Provisional Patent Application claims the benefit of the filing date of U.S. Provisional Patent Application Ser. No. 62/537,162, filed Jul. 26, 2017, entitled "RESILIENT TIP AND METHOD," and of U.S. Provisional Patent Application Ser. No. 62/643,929, filed Mar. 16, 2018, entitled "RESILIENT TIP AND METHOD," both of which are incorporated herein by reference.

BACKGROUND

One aspect relates to guidewires for interventional medical application. Typical guidewires that are stiff enough to push through vasculature and support subsequent delivery of devices utilize a full stainless steel core. Such stainless steel core wires, however, tend to have a thinner distal tip that tends to kink when bending. Because there are limitations to many present approaches, there is a need for the present embodiments.

BRIEF DESCRIPTION OF THE DRAWINGS

FIG. 1 illustrates a cross-sectional side view of proximal and distal sections of a guidewire in accordance with one embodiment.

FIG. 2 illustrates a cross-sectional side view of proximal and distal sections of a guidewire in accordance with one embodiment.

FIG. 3 illustrates a cross-sectional side view of proximal and distal sections of a guidewire in accordance with one embodiment.

FIG. 4 illustrates a cross-sectional side view of proximal and distal sections of a guidewire in accordance with one embodiment.

FIG. 5 illustrates a cross-sectional side view of proximal and distal sections of a guidewire in accordance with one embodiment.

DETAILED DESCRIPTION

Figure 6:
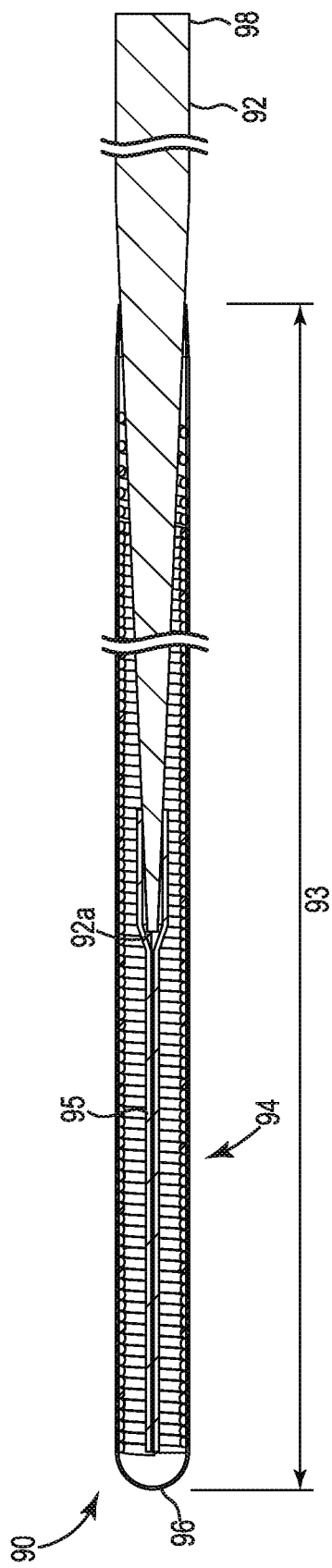
FIG. 6 illustrates a cross-sectional side view of proximal and distal sections of a guidewire in accordance with one embodiment.

In the following Detailed Description, reference is made to the accompanying drawings, which form a part hereof, and in which is shown by way of illustration specific embodiments. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope. The following detailed description, therefore, is not to be taken in a limiting sense, and the scope of the embodiments is defined by the appended claims.

One aspect of medical guidewires and related guiding members, whether they are formed of solid wire or tubular members, is that they have sufficient column strength and stiffness to be pushed through passageways in a patient, such as the patient's vascular system, with minimal kinking or binding. However, the distal tip section of the guidewire must also be flexible enough to avoid damaging the blood vessel or other body lumen through which it is advanced. Accordingly, efforts have been made to provide guidewires having a favorable combination of both strength and flexibility in order to make them suitable for their intended uses. However, strength for pushing and flexibility for turning without damaging vascular walls tend to be diametrically opposed to one another, such that an increase in one usually involves a decrease in the other, as exemplified below.

The cores of conventional guidewires have been made of many different materials. Two of the more popular materials are stainless steel and Nitinol. In particular, stainless steel has good pushability properties as well as good torque qualities. In turn, guidewire cores formed of such material are generally found suitable for being advanced, and further, for being rotated, so as aid in their being maneuvered, through a patient's vascular system. However, such steel core guidewires tend to be stiff, that is, not easily bent, and limited in their flexibility. As such, if the steel guidewire is not carefully used, the potential exists for damaging the vessel/body lumen through which it is being advanced. In addition, the steel can be found to bind or kink when severely bent since it does not readily flex. Once the guidewire is kinked, it must often be discarded and replaced with a new guidewire.

On the other hand, guidewires formed with Nitinol cores are found to have the flexibility that is warranted for negotiation through a tortuous path in a patient's body lumens or vessels. In turn, when being advanced through a patient's vascular system, such guidewires are found to exhibit lower potential for either damaging the patient's vessel/body lumen or kinking/binding. Unfortunately, such Nitinol guidewires are found to have insufficient stiffness. As such, they cannot be torqued as readily as stainless steel, thereby limiting their maneuverability. In addition, superelastic Nitinol guidewires tend to have good flexibility. Accordingly, they are found to have limited pushability against resistance of tortuosity (e.g., in comparison to guidewires having stainless steel cores) because they tend to be less stiff and flex during their advancement. The superelasticity and resistance to permanent deformation can make it difficult for a physician to shape the tip of the guidewire with his or her fingers for accessing difficult to reach portions of the patient's vascular system.

There has been a gradual decrease in the diameter profiles or transverse dimensions of commercially available guidewires such that these guidewires can be more universally applied in a wide variety of medical procedures, including interventional oncology, electrophysiology, peripheral, cardiac, urology, neurology, and gastroenterology. For example, when materials generally known to be rigid or stiff are formed to have decreased profiles, such materials (and the guidewires that they are used in forming) can be found to exhibit greater flexibility. However, associated with the decrease in profile has also been a general loss in pushability and an increase in kinking in the wire.

For example, a guidewire stiff enough to push through certain vasculature and support subsequent delivery of devices utilizes a full stainless steel core. In order to achieve sufficient flexibility of the distal tip section, however, the diameter of the distal tip section, or portion thereof, is narrowed, thereby making the distal tip section susceptible to kinking when prolapsing, or bending over on itself, occurs.

FIG. 1 illustrates guidewire 10 in accordance with one embodiment. Guidewire 10 includes core wire 12 and resilient portion 14. In one embodiment, core wire 12 extends from a proximal end 18 out to a distal end 16. In one embodiment, core wire 12 is a solid core along its entire length and is made of stainless steel, or one of a multitude of high-stiffness alloys that exhibit varying characteristics, such as, for example, a high-performance cobalt-based alloy 35N LT®. In one embodiment, resilient portion 14 overlaps core wire 12 in a distal tip section 13 of guidewire 10.

In one embodiment, for the majority of the length of the guidewire from the proximal end 18, the diameter of core wire 12 is sufficient to provide good pushability properties as well as good torque qualities. In addition, core wire 12 exhibits high stiffness such that it is generally suitable for being advanced, and further, for being rotated, so as aid in its being maneuvered, through a patient's vascular system. In the illustration, the guidewire 10 is shown with breaks or interruptions, because overall length of the guidewire 10 will vary, as will the relative lengths of core wire 12 and resilient portion 14, and accordingly the relative lengths of the various portions are not to scale.

In one embodiment, at least a portion of the core wire 12 near the distal end 16 is provided with a taper (shown in more detail in further figures and discussed below), to provide additional flexibility across at least distal tip section 13 of the guidewire 10. Normally, such a reduced diameter section also creates a general loss in pushability, and an increase in kinking in the core wire 12. In one embodiment, however, resilient portion 14 is added to core wire 12 at the distal tip section 13. The addition of resilient portion 14 adjacent distal end 16 in distal tip section 13 generally increases pushability and also withstands prolapse with minimal kinking in the core wire 12 in that area.

In one embodiment, resilient portion 14 is a superelastic material, such as Nitinol, Triton®, or another superelastic and/or Nitinol-based alloy, that is added to the distal tip section 13 of guidewire 10, such that the distal tip section 13 withstands prolapse with minimal kinking. Guidewires that include superelastic cores or that have bimetal construction, including superelastic portions, do not exhibit adequate stiffness in the primary core to reach certain target areas. But, guidewire 10, with solid core wire 12 having high stiffness, exhibits favorable handling characteristics and distal tip stiffness up to resilient portion 14. Furthermore, the amount of distal tip stiffness and overall handling characteristics of guidewire 10 can be varied by using a variety of grind profiles, diameters, flattened configurations, and assembly methods.

As illustrated in FIG. 1, in one embodiment, resilient portion 14 overlaps the entire distal tip section 13 of core wire 12, such that each of resilient portion 14 and core wire 12 terminate at the distal end 16. In one embodiment, a coil can be added over all, or over a portion, of the distal tip section 13 and/or a polymer layer can be added over resilient portion 14, core wire 12 and/or over the coil in the distal tip section 13. In one embodiment, resilient portion 14 is a relatively straight and long section of resilient material oriented generally parallel to core wire 12, such that there is surface contact between resilient portion 14 and core wire 12 substantially over the entire overlapping portions in the distal tip section 13. The relatively flat shape of resilient portion 14 generally increases pushability and also increases the ability of guidewire 10 to withstand prolapse with minimal kinking in the distal tip section 13.

Joining resilient portion 14 to core wire 12 at distal tip section 13 can be done in a variety of configurations. They can be joined using adhesive, solder, welding, mechanical swaging, insertion of dissimilar metals into a tube, or shrink fitting a polymer material over the joint.

In one embodiment, guidewire 10 has a total length between its proximal end 18 to its distal end 16 of between approximately 70 inches to 150 inches. In one embodiment, resilient portion 14 within distal tip section 13 is approximately from 0.05 inches to 2.0 inches in length. In one embodiment, the outer diameter of guidewire 10 ranges from about 0.005 to about 0.035 inches.

FIG. 2 illustrates guidewire 20 in accordance with one embodiment. Similar to guidewire 10, guidewire 20 includes core wire 22 and resilient portion 24. In one embodiment, core wire 22 is a solid core along its entire length and is made of stainless steel, or one of a multitude of high-stiffness alloys that exhibit varying characteristics, such as, for example, a high-performance cobalt-based alloy 35N LT®.

In one embodiment, guidewire 20 includes a first distal tip section 23a, where the core wire 22 overlaps with the resilient portion 24 and a second distal tip section 23b, where the resilient portion 24 extends from the first distal tip section 23a to the distal end 26. In one embodiment, core wire 22 extends from a proximal end 28 out through the first distal tip section 23a. In one embodiment, resilient portion 24 is a superelastic material, such as Nitinol, Triton®, or another superelastic and/or Nitinol-based alloy In one embodiment resilient portion 24 is added to core wire 22 at the first distal tip section 23a, and extends guidewire 20, via the second distal tip section 23b, out to a distal end 26 of guidewire 20. The addition of resilient portion 24 at distal tip sections 23a/23b generally increases pushability and withstands prolapse with minimal kinking in the core wire 22 in that area. In one embodiment, resilient portion 24 is a relatively straight and long section of resilient material oriented generally parallel to core wire 22, such that there is surface contact between resilient portion 24 and core wire 22 substantially over the entire overlapping portions in the distal tip section 23a, thereby increasing pushability and increasing the ability of guidewire 20 to withstand prolapse with minimal kinking in the distal tip section 23a/b.

In various embodiments, the amount of overlap between resilient portion 24 and core wire 22 can be varied to change the overall handling characteristics of guidewire 20. In various embodiments, the distance that resilient portion 24 overlaps with core wire 22 in first distal tip section 23a varies between 0.05 and 2.0 inches, and the distance that resilient portion 24 extends beyond core wire 22 in second distal tip section 23b varies between 0.05 and 2.0 inches.

As with guidewire 10 above, core wire 22 in one embodiment is a solid core along its entire length and is made of stainless steel. In one embodiment, for the majority of the length of the guidewire from the proximal end 28, the diameter of core wire 22 is sufficient to provide good pushability properties as well as good torque qualities. In addition, core wire 22 exhibits high stiffness such that it is generally suitable for being advanced, and further, for being rotated, so as aid in its being maneuvered, through a patient's vascular system. Also, at least a portion of the core wire 22 in the first distal tip section 23a is provided with a taper, to provide additional flexibility across at least that section of the guidewire 20.

Joining resilient portion 14, 24 of a superelastic material to the distal tip section 13, 23a/23b, allows the guidewire 10, 20 to withstand prolapse with minimal kinking. This allows for the repeated use of the guidewire 10, 20 within a procedure without having to re-shape or replace the guidewire 10, 20. Furthermore, there is reduced risk of loss of wire position, reduced case time, reduced cost and reduced fluoroscopy exposure. Compared to guidewires with bimetal transitions occurring mid-shaft, guidewires 10, 20 maximize stiffness and push-ability with minimal distal tip kinking. This reduced distal tip kinking results in more predictable guidewire steering.

FIG. 3 illustrates guidewire 30 in accordance with one embodiment. Similar to previously-described guidewires, guidewire 30 includes core wire 32 and resilient portion 34. In one embodiment, core wire 32 is a solid core along its entire length and is made of stainless steel, or one of a multitude of high-stiffness alloys that exhibit varying characteristics, such as, for example, a high-performance cobalt-based alloy 35N LT®.

In one embodiment, resilient portion 34 overlaps core wire 32 in a distal tip section 33 of guidewire 30. In one embodiment, core wire 32 extends from a proximal end 38 to a distal end 32a within distal tip section 33. In one embodiment, core wire 32 is tapered within distal tip section 33 in order to increase flexibility of guidewire 30 in that region. In one embodiment, a proximal side of distal tip section 33 begins where core wire 32 begins its taper and a distal side of distal tip section 33 coincides with distal end 36 of guidewire 30. In other embodiments, core wire 32 has more taper, less taper, or no taper.

In one embodiment resilient portion 34 is added to core wire 32 at distal tip section 33, and extends guidewire 30 out to a distal end 36 of guidewire 30. The addition of resilient portion 34 at distal tip section 33 generally increases push-ability and withstands prolapse with minimal kinking in the guidewire 30 in that area.

In one embodiment, resilient portion 34 includes first, second and third resilient segments 34a, 34b, and 34c. As illustrated in FIG. 3, first resilient segment 34a overlaps a top (as depicted in the figure) portion of the core wire 32 at distal tip section 33 and third resilient segment 34c overlaps a bottom (as depicted in the figure) portion of the core wire 32 at distal tip section 33, while second resilient segment 34b butts up against the distal end 32a of core wire 32 within distal tip section 33 and is sandwiched between the first and third resilient segments 34a and 34c. Each of the resilient segments 34a, 34b and 34c extend generally from the core wire 32, through distal tip section 33 and to the distal end 36 of guidewire 30. In one embodiment, first resilient segment 34a overlaps a larger portion of core wire 32 than does third resilient segment 34c, such that first resilient segment end 45a is further down core wire 32 (toward proximal end 38) than is third resilient segment end 45c. These staggered end locations 45a and 45c of first and third resilient segments 34a and 34c provide gradual and smooth transition of stiffness from the more flexible resilient portion 45 to the stiffer core wire 32 of the guidewire 30. In one embodiment, each of resilient segment 34a, 34b, 34c are a superelastic material, such as Nitinol, Triton®, or another superelastic and/or Nitinol-based alloy.

In one embodiment, each of first, second and third resilient segments 34a, 34b, 34c are relatively straight and long sections of resilient material, each oriented generally parallel to core wire 32. As such, that there is surface contact between resilient segments 34a and 34c and core wire 32 substantially over the entire overlapping portions in the distal tip section 33, thereby increasing pushability and increasing the ability of guidewire 30 to withstand prolapse with minimal kinking in the distal tip section 33.

In one embodiment, radiopaque coil 42 and polymer jacket 44 are added over the resilient portion 34 and overlap the core wire 32 in distal tip section 33. In other embodiments, other types of coils are used, or no coil is used. In one embodiment, the radiopaque coil 42 and/or polymer jacket 44 thickness can be tapered to match tapering of the layers over which they are placed such that guidewire 30 has a relatively constant outer diameter along its axial length.

Using these additional multiple strips of flat or round, relatively straight wire resilient segments 34a, 34b, 34c allow for manipulation and modification of the resiliency and kink properties of the resilient portion 34 of the guidewire distal tip. Various embodiments of guidewire 30 use a variety of configurations and components for resilient portion 34. For example, guidewire 30 can use a range of quantities (e.g., 1-4) of resilient segments attached to, or adjacent to, core wire 32, use various sizes of resilient segments (e.g., 0.001-0.030 inches), use various cross-sectional shapes (e.g., round, oval, rectangular, tubular, etc.), use various alloys (e.g., NiTi, NiTiCo, Titanium, annealed stainless steel, etc.), and use various configurations (in one plane, circumferentially located on the core wire, etc.). Also, radiopaque coil 42 and polymer jacket 44 can be optionally added the resilient portion 34. In one embodiment, coils are added in the resilient portion 34, but no polymer jacket is added at all. In yet other embodiments, neither coils nor polymer jackets are added to the resilient portion 34. Varying these added components or resilient segments modify the tip bending characteristics. In order to achieve the increased pushability and withstanding of prolapse with minimal kinking in the guidewire 30, at least one relatively straight and long resilient segment 34a, 34b or 34c should be added to resilient portion 34.

FIG. 4 illustrates guidewire 50 in accordance with one embodiment. Similar to previously-described guidewires, guidewire 50 includes core wire 52 and resilient portion 54. In one embodiment, core wire 52 is a solid core along its entire length and is made of stainless steel, or one of a multitude of high-stiffness alloys that exhibit varying characteristics, such as, for example, a high-performance cobalt-based alloy 35N LT®.

In one embodiment, resilient portion 54 overlaps core wire 52 in a distal tip section 53 of guidewire 50. In one embodiment, core wire 52 extends from a proximal end 58 to a distal end 52a within distal tip section 53. In one embodiment, core wire 52 is tapered within distal tip section 53 in order to increase flexibility of guidewire 50 in that region. In one embodiment, a proximal side of distal tip section 53 begins where core wire 52 begins its taper and a distal side of distal tip section 53 coincides with distal end 56. In other embodiments, core wire 52 has more taper, less taper, or no taper.

In one embodiment resilient portion 54 is added to core wire 52 at the distal tip section 53, and extends guidewire 50 out to a distal end 56 of guidewire 50. In one embodiment, the addition of resilient portion 54 to core wire 52 generally provides certain zones designed to kink, or prolapse, earlier than other zones, resulting in a wire that prolapses in a predictable way.

Similar to guidewire 30 above, resilient portion 54 includes first resilient segment 54a that overlaps a top (as depicted in the figure) portion of the core wire 52 at core wire distal tip section 60 and second resilient segment 54b that overlaps a bottom (as depicted in the figure) portion of the core wire 52 within distal tip section 53. In one embodiment, first and second resilient segments 54a/b overlap unequal portions of core wire 52, such that they are staggered. In one embodiment, there is no additional resilient segment between them, such that there is a gap between first and second resilient segments 54a/b from the distal end 52a of core wire 52 to the distal end 56. In one embodiment, each of resilient segments 54a/b are a superelastic material, such as Nitinol, Triton®, or another superelastic and/or Nitinol-based alloy.

In one embodiment, each of first and second resilient segments 54a and 54b are relatively straight and long sections of resilient material, each oriented generally parallel to core wire 52. As such, that there is surface contact between resilient segments 54a and 54b and core wire 52 substantially over the entire overlapping portions in the distal tip section 53, thereby increasing pushability and increasing the ability of guidewire 50 to withstand prolapse with minimal kinking in the distal tip section 53.

In one embodiment, while second resilient segment 54b extends generally from the core wire 52 to the distal end 56 of guidewire 50, first resilient segment 54a terminates at radiopaque coil 62. This termination of first resilient segment 54a creates intentional prolapse zone 55. In one embodiment, the inclusion of intentional prolapse zone 55 in the resilient portion 54 creates a predictable prolapse feature, with this zone that is more susceptible to bending, which may have advantages in certain applications.

In any of the embodiments herein, the resilient segments may have varying configuration and characteristics. For example, the following parameters may be used for the resilient portions:

- The flat wires may vary in thickness from 0.0005-0.010 inches, and may vary in width from 0.002-0.030 inches, depending on the guidewire size and performance.
- Round wires may vary in diameter from 0.0005-0.020 inches, depending on the guidewire size and performance.
- Wire lengths for the resilient segments may vary from 0.25-10.0 inches, depending on the guidewire size and performance.
- Wires for the resilient segments may be attached to core wire with adhesive, solder, weld, press fit or using a temperature enhanced press fit method.
- The proximal core wire could be manufactured from stainless steel, 35NLT (cobalt chrome alloy) or other high performance (relatively stiff) material.
- Wires can overhang distally beyond the guidewire core tip, be flush or proximal to guidewire core tip depending on desired performance.
- Round wires may be fully or partially flattened at the distal section to enhance the guidewire performance and offer a variety of tip flexibility and resiliency.

FIG. 5 illustrates guidewire 70 in accordance with one embodiment. Similar to previously-described guidewires, guidewire 70 includes core wire 72 and resilient portion 74. In one embodiment, core wire 72 is a solid core along its entire length and is made of stainless steel, or one of a multitude of high-stiffness alloys that exhibit varying characteristics, such as, for example, a high-performance cobalt-based alloy 35N LT®.

In one embodiment, resilient portion 74 overlaps core wire 72 in a distal tip section 73 of guidewire 70. In one embodiment, core wire 72 extends from a proximal end 78 to a distal end 72a within distal tip section 73. In one embodiment, core wire 72 is tapered within distal tip section 73 in order to increase flexibility of guidewire 70 in that region. In one embodiment, a proximal side of distal tip section 73 begins where core wire 72 begins its taper and a distal side of distal tip section 73 coincides with distal end 76. In other embodiments, core wire 72 has more taper, less taper, or no taper.

In one embodiment resilient portion 74 is added to core wire 72 at the distal tip section 73, and extends guidewire 70 out to a distal end 76 of guidewire 70. In one embodiment, the addition of resilient portion 74 to core wire 72 generally provides reduced distal tip kinking results in more predictable guidewire steering.

In one embodiment, resilient portion 74 includes hypotube 75, which is placed over a distal end 72a of core wire 72. In one embodiment, core wire 72 has a tapered diameter in distal tip section 73 such that hypotube 75 can be slid over the core wire 72, such that there is overlap as illustrated in FIG. 5. In one embodiment, radiopaque coil 82 and polymer jacket 84 are added over the hypotube 75 and overlap the core wire 72 in the distal tip section 73.

In various embodiments, hypotube 75 is any of various alloys, including NiTi, NiTiCo, or is Titanium or annealed stainless steel. Hypotube 75 can be secured to core wire 72 in various ways. In one embodiment, hypotube 75 can be filled with an adhesive and slid over core wire 72. In other embodiments, hypotube 75 can be attached to core wire 72 using solder, welding, mechanical swaging, insertion of dissimilar metals into a tube, or shrink fitting a polymer material.

Figure 7:
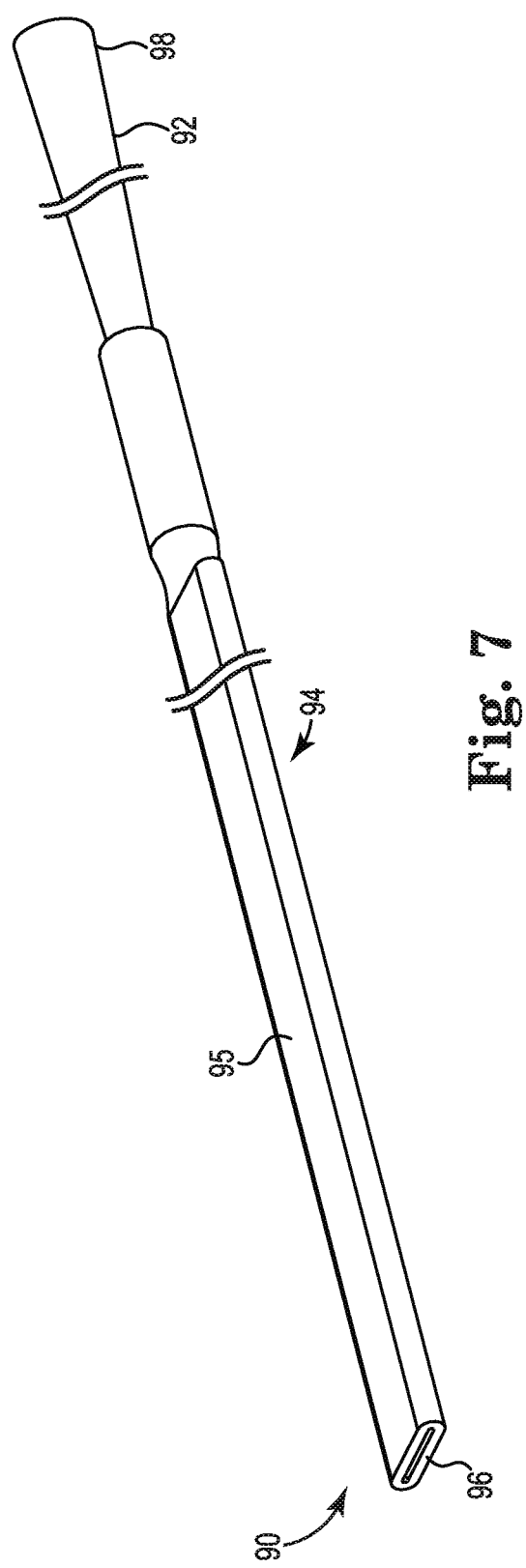
FIG. 7 illustrates an oblique view of proximal and distal sections of a guidewire in accordance with one embodiment.

FIGS. 6 and 7 illustrates guidewire 90 in accordance with one embodiment. FIG. 6 illustrates a sectional view, while FIG. 7 is a perspective view. Similar to previously-described guidewire 70, guidewire 90 includes core wire 92 and resilient portion 94. In one embodiment, core wire 92 is a solid core along its entire length and is made of stainless steel, or one of a multitude of high-stiffness alloys that exhibit varying characteristics, such as, for example, a high-performance cobalt-based alloy 35N LT®.

In one embodiment, resilient portion 94 overlaps core wire 92 in a distal tip section 93 of guidewire 70. In one embodiment, core wire 92 extends from a proximal end 98 to a distal end 92a within distal tip section 93. In one embodiment, core wire 92 is tapered within distal tip section 93 in order to increase flexibility of guidewire 90 in that region. In one embodiment, a proximal side of distal tip section 93 begins where core wire 92 begins its taper and a distal side of distal tip section 93 coincides with distal end 96. In other embodiments, core wire 92 has more taper, less taper, or no taper.

In one embodiment, core wire 92 extends from a proximal end 98 into a distal tip section 93. In one embodiment resilient portion 94 is added to core wire 92 at the distal tip section 93, and extends guidewire 90 out to a distal end 96 of guidewire 90. In one embodiment, the addition of resilient portion 94 at distal tip section 93 generally provides reduced distal tip kinking results in more predictable guidewire steering.

In one embodiment, resilient portion 94 includes hypotube 95, which is placed over core wire 92 within distal tip section 93. In one embodiment, hypotube 95 is slid over core wire 92, and then is flattened over the distal end 92a of core wire 92. In one embodiment, hypotube 95 is also flattened over its entire remaining length out to the distal end 96 of guidewire 90. Flattening at the distal end 96 in this way will modify the tip flex properties, which is advantageous in some embodiments. In one embodiment, hypotube 95 is flattened only in the portion where it overlaps with core wire 92. In one embodiment, a portion of hypotube 95 that extends distally from core wire 92 is also flattened, and in another, the entire hypotube 95 is flattened.

In any of the embodiments herein, the hypotube of the resilient portion may have varying configuration and characteristics. For example, the following parameters may be used for the hypotube:

The tube diameter may vary from 0.002-0.030 inches for inner diameter, depending on the guidewire size and performance.

The tube wall thickness may vary from 0.0005-0.005 inches, depending on the guidewire size and performance.

The tube lengths may vary from 0.25-10.0 inches, depending on the guidewire size and performance.

The tube may be attached to core with adhesive, solder, weld, press fit or using a temperature enhanced press fit method.

A flattened section may be used, and the flattened section may vary in thickness, width, and length, depending on guidewire size and performance.

The proximal core wire could be manufactured from stainless steel, 35NLT (cobalt chrome alloy) or other high performance (relatively stiff) material.

The tube can overhang distally beyond the guidewire core tip, be flush or proximal to guidewire core tip depending on desired performance.

The tube can be fully or partially flattened to enhance the guidewire performance.

Furthermore, with any of the above-described embodiments, portions of any of the guidewires that have superelastic properties, e.g., Nitinol, NiTiCo, etc., can be annealed or semi-annealed, so that those portions can have a bend or kink introduced, which may be favorable feature in some applications. For example, in the embodiment of FIGS. 6-7, where the resilient portion 94 includes hypotube 95 placed over core wire 92 in distal tip section 93, the hypotube may have superelastic properties, such that can readily be annealed or semi-annealed, so that those it can have a bend or kink introduced where advantageous to the user.

Although specific embodiments have been illustrated and described herein, it will be appreciated by those of ordinary skill in the art that a variety of alternate and/or equivalent implementations may be substituted for the specific embodiments shown and described without departing from the scope. This application is intended to cover any adaptations or variations of the specific embodiments discussed herein, and the equivalents thereof.

What is claimed is:

1. A medical guidewire comprising:
a core wire comprising a proximal end extending out to a distal end; and
a resilient portion coupled to and overlapping with the distal end of the core wire at a distal tip section of the guidewire;
wherein the resilient portion comprises a superelastic material and comprises a first and a second resilient segment; and
wherein each of the first and second resilient segments of the resilient portion comprise a one-piece, non-coiled section of resilient material, at least part of which is oriented parallel to the core wire, wherein the first and second resilient segments are attached to the core wire exclusively at an outer surface of the core wire and are staggered relative to each other, wherein there is surface contact between the first resilient segment and the core wire over an entire overlapping portion of the first resilient segment and the core wire and surface contact between the second resilient segments and the core wire over an entire overlapping portion of the second resilient segments and the core wire, and wherein the one-piece, non-coiled sections of the first and second resilient segments increase pushability and increase the ability pushability to withstand prolapse with minimal kinking in the distal tip section.

2. The medical guidewire of claim 1, wherein the core wire comprises one of a solid stainless steel, solid stainless steel alloy, and solid cobalt-based alloy.

3. The medical guidewire of claim 1, wherein the resilient portion comprises one of nitinol, a superelastic alloy and a nitinol-based alloy.

4. The medical guidewire of claim 1, wherein the amount of overlap between the resilient portion and the core wire is between 0.05 and 2.0 inches.

5. The medical guidewire of claim 1, wherein the first resilient segment overlaps a larger portion of the core wire than the second resilient segment.

6. The medical guidewire of claim 1, wherein the first resilient segment overlaps the core wire at a first location and the second resilient segment overlaps the core wire at a second location such that there is a gap between the first and second segments distal to the distal end of the core wire.

7. The medical guidewire of claim 1, wherein the resilient portion is fixed to the core wire such that the distal end of the core wire and a distal end of the resilient portion coincide with a distal end of the guidewire.

8. The medical guidewire of claim 1, wherein the resilient portion is fixed to the core wire such that an end of the resilient portion extends beyond the distal end of the core wire such that the end of the resilient portion defines a distal end of the guidewire.

9. The medical guidewire of claim 1, wherein the resilient portion is fixed to the core wire with adhesive, solder, welding, mechanical swaging, insertion of dissimilar metals into a tube, or shrink fitting a polymer material over a joint between the resilient portion and the core wire.

10. A method of forming a medical guidewire comprising:
providing a core wire comprising a proximal end extending to a distal end; and
coupling a resilient portion adjacent to and overlapping with the distal end of the core wire to form a distal tip section of the guidewire;
wherein the resilient portion comprises a superelastic material and comprises a first and a second resilient segment; and
wherein each of the first and second resilient segments of the resilient portion comprise a one-piece, non-coiled section of resilient material at least part of which is oriented parallel to the core wire, wherein the first and second resilient segments are attached to the core wire exclusively at an outer surface of the core wire and are staggered relative to each other, wherein there is surface contact between the first resilient segment and the core wire over an entire overlapping portion of the first resilient segment and the core wire and surface contact between the second resilient segments and the core wire over an entire overlapping portion of the second resilient segments and core wire wherein the one-piece, non-coiled sections of the first and second resilient segments increase pushability and increase the ability pushability to withstand prolapse with minimal kinking in the distal tip section.

11. The method of claim 10, wherein the resilient portion is coupled to the core wire such that they overlap by between 0.05 and 2.0 inches.

12. The method of claim 10, wherein the resilient portion is fixed to the core wire with adhesive, solder, welding, mechanical swaging, insertion of dissimilar metals into a tube, or shrink fitting a polymer material over a joint between the resilient portion and the core wire.

13. The method of claim 10, wherein the core wire comprises stainless steel, stainless steel alloy, or cobalt-based alloy.

14. The method of claim 10, wherein the resilient portion comprises one of nitinol, a superelastic alloy and a nitinol-based alloy.

* * * * *